US00PP23172P3

(12) United States Plant Patent
Korlipara

(10) Patent No.: US PP23,172 P3
(45) Date of Patent: Nov. 6, 2012

(54) ***ECHINACEA* PLANT NAMED 'MAMA MIA'**

(50) Latin Name: ***Echinacea* spp.**
Varietal Denomination: Mama Mia

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 117 days.

(21) Appl. No.: 12/932,496

(22) Filed: Feb. 25, 2011

(65) Prior Publication Data

US 2012/0222183 P1 Aug. 30, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu

(74) *Attorney, Agent, or Firm* — Klarquist Sparkman, LLP

(57) ABSTRACT

A new and distinct *Echinacea* plant named 'Mama Mia' characterized by large inflorescences, bicolor ray florets that change color with maturity giving multiple colors on one plant—from orange to red orange to red purple, a medium large habit with excellent branching, numerous, strong stems, and excellent vigor.

1 Drawing Sheet

Botanical denomination: *Echinacea* spp.
Variety designation: 'Mama Mia'.

The present invention relates to a new and distinct cultivar of *Echinacea* and given the cultivar name 'Mama Mia'. *Echinacea* is in the family Asteraceae. This new cultivar is a third generation seeding originating from a planned breeding program using *Echinacea paradoxa* as the seed parent in the original cross and *Echinacea purpurea* 'Ruby Giant' (an unpatented plant) as the pollen parent. The exact parents of this selection are unknown, unnamed, proprietary plants.

Compared to *Echinacea* 'Evan Saul' also known as Sundown (U.S. Plant Pat. No. 17,659), the new cultivar has larger inflorescences with more intense color on the ray florets and is taller.

This new *Echinacea* cultivar is distinguished by:

1. large inflorescences,
2. bicolor ray florets that change color with maturity giving multiple colors on one plant—from orange to red orange to red purple,
3. a medium large habit with excellent branching,
4. numerous, strong stems, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences and habit of *Echinacea* 'Mama Mia' as one year old plants growing in the field in full sun in early July in Canby, Oreg.

DETAILED PLANT DESCRIPTION

The following is a detailed description of the new *Echinacea* cultivar based on observations of 18 month-old specimens growing in 2 gallon pots in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 41 cm wide and 71 cm tall to top of inflorescences.
*Form.*—Basal clump, with about 11 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 3 flowers per stem.
*Size.*—To 69 cm tall to a terminal inflorescence and 8 mm wide at base.
*Internode length.*—1 cm to 5 cm.
*Surface texture.*—Strigose.
*Color.*—Greyed Purple 187A on bottom half and Yellow Green 147B tinted with Greyed Purple 187A on top half.

Leaf (basal):

*Type.*—Simple.
*Shape.*—Ovate.
*Arrangement.*—Basal.
*Blade size.*—Grows to 9 cm long and 5 cm wide.
*Margins.*—Serrate.
*Apex.*—Acute.
*Base.*—Attenuate.
*Surface texture.*—Strigose on both sides.
*Venation.*—Pinnate, with 3 main veins.

*Color.*—Topside Green 137B, bottom side Yellow Green 147B.

*Petiole description.*—Grows to 16.5 cm long and 2 mm wide, strigose, Yellow Green 147B near blade to Greyed Purple 187A near base.

Leaf (stem):

*Type.*—Simple.

*Shape.*—Ovate to lanceolate.

*Arrangement.*—Alternate.

*Blade size.*—Grows to 11 cm long and 4.5 cm wide.

*Margins.*—Serrate.

*Apex.*—Acute to acuminate.

*Base.*—Attenuate.

*Surface texture.*—Strigose on both sides.

*Venation.*—Pinnate, with 3 main veins from the base.

*Color.*—Topside Green 137A bottom side Yellow Green 147B.

*Petiole description.*—On lowermost leaves only, clasping, grows to 7 cm long and 5 mm wide above the clasp, scabrous, Yellow Green 147B infused with Greyed Purple 187A.

Inflorescence:

*Type.*—Composite on terminal stalked heads.

*Number of flowering stems per plant.*—About 11.

*Flowering stem.*—Grows to 69 cm tall from the base of the plant to the terminal inflorescence and can grow to 20 cm long from the top stem leaf to the base of an inflorescence; branched, with 1 to 3 inflorescences per stem; diameter growing to 9 mm wide near the inflorescence; strigose; Yellow Green 147B mottled Greyed Purple 187A.

*Size.*—Grows to 12 cm wide and 6 cm deep as disc enlarges.

*Form.*—Ray florets held slightly reflexed, mature disc is conic.

*Immature inflorescence.*—Grows to 3 cm wide and 2.5 cm deep, ray florets held upright and rolled up so only the back color shows, Yellow 18B, disc color Yellow Green 147A.

*Ray florets.*—Without pistil or stamen, about 23 full size (and 0 to 7 smaller rays growing at irregular angles), grow to 5 mm long and 15 mm wide, sometimes cupped down, oblanceolate with the tip two-toothed (each acute), entire margins, base attenuate, glabrous on both sides; topside newly opened Greyed Orange 170A to Red 53C at base, mature florets topside Greyed Red 182A with Red 53A on bottom half, older florets topside, Greyed Purple 185C with Red Purple 59A at base; bottom side Red Purple 70A at all stages.

*Disc.*—Flat becoming conic, becoming 35 mm deep and 45 mm wide with maturity, Orange 25B to Greyed Purple 187A.

*Disc florets.*—About 400 in number, each with 1 pistil and 4 stamen, grow to 9.5 mm long and 1.5 mm wide, each with one persistent, very stiff linear bract (15 mm long with the tip Greyed Purple 187A to top 3 mm colored Orange 25A to Greyed Purple N186C to Green 137C to White NN155A on bottom ⅓); corolla 5.5 mm long and 1.5 mm wide, tubular, 5 lobed, glabrous, Green 137C on bottom half and darkening to Greyed Purple N186C on lobes; pistil 10 mm long, ovary 3 mm long, White NN155D, style 6 mm long Yellow Green 145C, 2-branched stigma spreading 4 mm wide, Greyed Purple 187A; stamen 8 mm long, filaments 4 mm long and Yellow Green 145D, anthers 3 mm long and Grey Brown 199A, pollen Yellow Orange 21A.

*Phyllaries.*—In 4 leafy series, area grows to 35 mm wide and 10 mm deep, lobes lanceolate in shape, reflexed, grow to 15 mm long and 4.5 mm wide, Yellow Green 147B, margins strigose, tip acute, strigose on both sides.

*Receptacle.*—Grows to 15 mm wide and 21 mm deep, White 155B.

*Bloom period.*—July through October in Canby, Oreg.

*Fragrance.*—Sweet, floral.

*Lastingness.*—Each inflorescence lasts about two weeks in Canby, Oreg.

Seeds: 3 mm long and 2.5 mm wide, oval, Brown 200C.

*Fertility.*—Fair.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

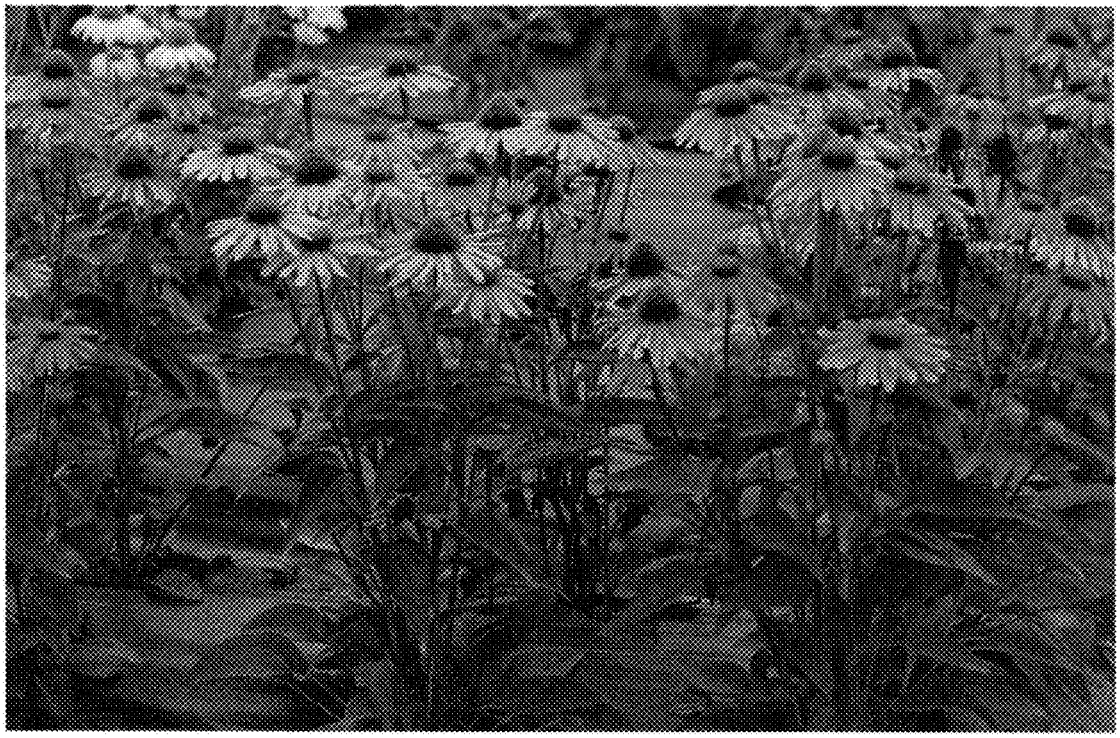

* * * * *